US009245435B2

(12) United States Patent
Boone

(10) Patent No.: US 9,245,435 B2
(45) Date of Patent: Jan. 26, 2016

(54) GAS DETECTOR CONTROL SYSTEM AND METHOD

(75) Inventor: Christopher N. Boone, Middletown, CT (US)

(73) Assignee: Honeywell International Inc., Morristown, NJ (US)

( * ) Notice: Subject to any disclaimer, the term of this patent is extended or adjusted under 35 U.S.C. 154(b) by 402 days.

(21) Appl. No.: 13/370,111

(22) Filed: Feb. 9, 2012

(65) Prior Publication Data

US 2012/0212347 A1 Aug. 23, 2012

Related U.S. Application Data

(60) Provisional application No. 61/444,913, filed on Feb. 21, 2011.

(51) Int. Cl.
| | |
|---|---|
| G08B 17/10 | (2006.01) |
| G08B 21/12 | (2006.01) |
| H04W 4/04 | (2009.01) |
| G08B 29/20 | (2006.01) |
| G01N 33/00 | (2006.01) |

(52) U.S. Cl.
CPC ............ *G08B 21/12* (2013.01); *G01N 33/0075* (2013.01); *G08B 29/20* (2013.01); *H04W 4/043* (2013.01)

(58) Field of Classification Search
CPC ..... G08B 21/12; G08B 29/20; G01N 33/0075
USPC ............ 340/539.11–14, 539.22, 539.26, 340/539.29, 632–634; 600/300, 30
See application file for complete search history.

(56) References Cited

U.S. PATENT DOCUMENTS

| | | | |
|---|---|---|---|
| 6,442,639 B1* | 8/2002 | McElhattan et al. | 710/303 |
| 7,089,780 B2* | 8/2006 | Sunshine et al. | 73/23.2 |
| 7,945,471 B2* | 5/2011 | McKinney et al. | 340/870.03 |
| 8,560,250 B2* | 10/2013 | Connolly et al. | 702/32 |
| 2002/0178789 A1 | 12/2002 | Sunshine et al. | |
| 2006/0192680 A1* | 8/2006 | Scuka et al. | 340/632 |
| 2008/0122641 A1* | 5/2008 | Amidi | 340/632 |
| 2010/0212395 A1 | 8/2010 | Willett et al. | |
| 2011/0037571 A1* | 2/2011 | Johnson et al. | 340/10.5 |
| 2011/0037599 A1* | 2/2011 | Johnson, Jr. et al. | H04W 4/043 340/632 |

FOREIGN PATENT DOCUMENTS

WO WO 01/82063 A1 11/2001

OTHER PUBLICATIONS

European Search Report and Annex, dated May 10, 2012, corresponding to Application No. EP 12 15 6235.
Sperian Instrumentation—Reference Manual IQ System Database Manager Pro Software—P/N 13-241 Version 5.00 (Jun. 26, 2008).
Sperian Instrumentation—Reference Manual IQ Express™ Docking Station for ToxiPro®, ToxiLtd® & Toxi3Ltd™—Part No. 13-275, Version 4.04 (Feb. 17. 2011).

* cited by examiner

*Primary Examiner* — Benjamin C. Lee
*Assistant Examiner* — Chico A Foxx
(74) *Attorney, Agent, or Firm* — Conley Rose, P.C.; Kristin Jordan Harkins

(57) ABSTRACT

A gas detector management system includes a plurality of docking stations distributed in a region being monitored. One or more gas detectors in the region, which have been exposed to various gas concentrations, and which include respective stored maximum concentrations can be coupled to respective docking stations. Information including the maximum stored concentrations can be downloaded to the stations. Alert messages can be automatically generated and transmitted to displaced safety officer for follow-up.

10 Claims, 6 Drawing Sheets

INSTRUMENT USAGE REPORT
SORTED BY SERIAL NUMBER, DATE

| SERIAL NUMBER | USER | TYPE | LOCATION | CHECK OUT DATE | CHECK IN DATE |
|---|---|---|---|---|---|
| 000082619 | | PHD6 | | | |
| | WILSON, DAVID | | SOFTWARE ENGINEERING | 1/13/2010 09:00:00 AM | TO 09:00:00 AM |
| | BOONE, CHRIS | | SOFTWARE ENGINEERING | 3/12/2010 05:00:00 PM | TO 05:05:55 PM |
| | BASOLE, ANAGHA | | INSTRUMENT SERVICE | 3/15/2010 09:15:51 AM | TO 11:54:19 AM |
| | BASOLE, ANAGHA | | ENGINEERING | 4/21/2010 02:46:00 PM | STILL CHECKED OUT |
| 0001123569 | | TOXIPRO | | | |
| | ULIASZ, STEVE | | ENGINEERING | 7/07/2010 04:33:50 PM | TO 7/28/2010 10:44:44 AM |
| | ALLAN, NEIL | | ENGINEERING | 7/28/2010 10:44:44 AM | TO 6/07/2011 01:12:51 PM |
| | SAUBESTRE, PAUL | | ENGINEERING | 6/07/2011 01:12:51 PM | STILL CHECKED OUT |
| 00034 | | TOXILTD | | | |
| | ROY, PATRICIA | | INSTRUMENT SERVICE | 2/15/2010 09:00:51 AM | TO 02:54:19 PM |
| | SMITH, STEVE | | ENGINEERING BACK ROO | 2/19/2010 09:00:51 AM | TO 02:54:19 PM |
| | BASOLE, ANAGHA | | INSTRUMENT SERVICE | 2/24/2010 09:00:51 AM | TO 02:54:19 PM |
| 00420 | | TOXIPRO | | | |
| | SANGSTER, RICK | | UNKNOWN (3) | 1/16/2010 09:00:00 AM | TO 09:00:00 AM |
| | KAI, JOYCE | | ENGINEERING BACK ROO | 1/20/2010 09:00:00 AM | TO 09:00:00 AM |
| | EMOND, JEFF | | INSTRUMENT SERVICE | 3/12/2010 03:40:00 PM | TO 05:05:55 PM |
| | SAUBESTRE, PAUL | | ENGINEERING BACK ROO | 3/12/2010 04:00:00 PM | TO 05:05:55 PM |
| | UNASSIGNED | | ENGINEERING | 4/14/2010 04:36:23 PM | TO 04:44:34 PM |

| | | |
|---|---|---|
| UNASSIGNED | UNASSIGNED | 4/14/2010 04:44:34 PM TO 4/15/2010 10:19:47 AM |
| SAUBESTRE, PAUL | SOFTWARE ENGINEERING | 4/15/2010 10:19:47 AM TO 10:21:20 AM |
| SANGSTER, RICK | UNASSIGNED | 4/16/2010 01:14:14 PM TO 01:19:33 PM |
| SANGSTER, RICK | ENGINEERING | 4/16/2010 01:19:33 PM TO 4/19/2010 09:45:09 AM |
| BOONE, CHRIS | ENGINEERING | 4/19/2010 09:46:04 AM TO 4/20/2010 01:09:18 PM |
| DAVIDSON, KEN | ENGINEERING | 4/20/2010 01:09:18 PM TO 4/26/2010 11:40:18 AM |
| SMITH, STEVE | UNKNOWN (7) | 4/26/2010 11:40:18 AM TO 7/07/2010 04:34:16 PM |
| SAUBESTRE, PAUL | UNASSIGNED | 7/07/2010 04:34:16 PM TO 04:34:23 PM |
| UNASSIGNED | UNKNOWN (3) | 7/07/2010 04:34:40 PM TO 04:34:56 PM |
| SAUBESTRE, PAUL | UNKNOWN (3) | 7/07/2010 04:34:56 PM TO 6/07/2011 01:13:47 PM |
| SAUBESTRE, PAUL | ENGINEERING BACK ROO | 6/07/2011 01:13:47 PM **STILL CHECKED OUT ** |

| 0110450222 | IQ FORCE | |
|---|---|---|
| UNASSIGNED | UNASSIGNED | ** NO CHECKOUT HISTORY * |

| 020202020 | TOXIPRO | |
|---|---|---|
| BOONE, CHRIS | INSTRUMENT SERVICE | 4/26/2010 11:43:13 AM TO 7/07/2010 04:35:13 PM |
| SANGSTER, RICK | INSTRUMENT SERVICE | 7/07/2010 04:35:13 PM **STILL CHECKED OUT ** |

| 10450223 | IQ FORCE | |
|---|---|---|
| UNASSIGNED | UNASSIGNED | ** NO CHECKOUT HISTORY * |

| 109270466 | TOXIPRO | |
|---|---|---|
| KAI, JOYCE | SOFTWARE ENGINEERING | 1/21/2010 09:00:00 AM TO 09:00:00 AM |
| BOONE, CHRIS | UNKNOWN (3) | 3/15/2010 09:30:51 AM TO 11:54:19 AM |

*FIG. 3B*

ALARM REPORT
SPECIFIED SERIAL NUMBERS
SORTED BY SERIAL NUMBER, DATE

| SERIAL NUMBER | TYPE | USER MAX | LOCATION MIN | DURATION AVERAGE | ALARMS | START | | STOP | |
|---|---|---|---|---|---|---|---|---|---|
| 109371176 | TOXIPRO | | | | | | | | |
| 109371176 | TOXIPRO CO | BOONE, CHRIS 50 | ENGINEERING | 01:00 | WARNING | 6/21/2010 | 04:38:36 PM | TO | 04:39:36 PM |
| 109371176 | TOXIPRO CO | BOONE, CHRIS 50 | ENGINEERING | 47 | DANGER | 6/21/2010 | 04:38:45 PM | TO | 04:39:33 PM |
| 109371176 | TOXIPRO CO | BOONE, CHRIS 50 | ENGINEERING | 48 | CUSTOM | 6/21/2010 | 04:38:58 PM | TO | 04:39:00 PM |
| 109371176 | TOXIPRO CO | BOONE, CHRIS 49 | ENGINEERING | 49 02 | WARNING | 6/30/2010 | 02:09:53 PM | TO | 02:11:05 PM |
| 109371176 | TOXIPRO CO | BOONE, CHRIS 49 | ENGINEERING | 01:12 41 | DANGER | 6/30/2010 | 02:09:57 PM | TO | 02:10:51 PM |
| 109371176 | TOXIPRO CO | BOONE, CHRIS 49 | ENGINEERING | 54 45 | CUSTOM | 6/30/2010 | 02:10:03 PM | TO | 02:10:39 PM |
| 109371176 | TOXIPRO CO | BOONE, CHRIS 49 | ENGINEERING | 36 48 | WARNING | 6/30/2010 | 02:31:12 PM | TO | 02:32:26 PM |
| 109371176 | TOXIPRO CO | BOONE, CHRIS 50 | ENGINEERING | 01:14 44 | DANGER | 6/30/2010 | 02:31:16 PM | TO | 02:32:18 PM |
| 109371176 | TOXIPRO CO | BOONE, CHRIS 50 | ENGINEERING | 01:02 46 | CUSTOM | 6/30/2010 | 02:31:23 PM | TO | 02:32:04 PM |
| 109371176 | TOXIPRO CO | BOONE, CHRIS 50 | ENGINEERING | 41 49 | WARNING | 6/30/2010 | 02:48:15 PM | TO | 02:49:05 PM |
| 109371176 | TOXIPRO CO | BOONE, CHRIS 49 | ENGINEERING | 50 44 | DANGER | 6/30/2010 | 02:48:18 PM | TO | 02:49:02 PM |
| 109371176 | TOXIPRO CO | BOONE, CHRIS 49 | ENGINEERING | 44 46 | WARNING | 6/30/2010 | 03:35:38 PM | TO | 03:37:00 PM |
| 109371176 | TOXIPRO CO | BOONE, CHRIS 49 | ENGINEERING | 01:22 39 | DANGER | 6/30/2010 | 03:35:41 PM | TO | 03:36:34 PM |

13 TOTAL EVENTS    1 SERIAL NUMBERS    1 USERS    1 LOCATIONS

*FIG. 4*

| | | | | | |90|
|---|---|---|---|---|---|---|

IQ ALARM EVENT:
USER:               BOONE, CHRIS
LOCATION:           ENGINEERING
TOXIPRO SERIAL #:   110194223

| DATE | DURATION | TYPE | SENSOR | MAX | AVG |
|---|---|---|---|---|---|
| 06/30/2010 2:48:18 AM | 1:22 | DANGER | CO | 49 ppm | 46 ppm |
| 06/30/2010 3:35:41 AM | 0:53 | DANGER | CO | 49 ppm | 44 ppm |

*FIG. 5*

GAS DETECTOR CONTROL SYSTEM AND METHOD

CROSS-REFERENCE TO RELATED APPLICATION

This application claims the benefit of the filing date of U.S. Provisional Application Ser. No. 61/444,913 filed Feb. 21, 2011, entitled, "Gas Detector Control System and Method. The '913 application is hereby incorporated herein by reference.

FIELD

The application pertains to control systems and methods of managing large numbers of gas detectors used in monitoring exposure of individuals in regions of interest. More particularly, the application pertains to such systems and methods which provide prompt and automatic reporting of exposure of individuals to selected levels of a gas in a region of interest.

BACKGROUND

Systems are known to manage large numbers of gas detectors used in monitoring the exposure of individuals to one or more gases working in a region of interest. Docking stations are provided to enable detector users to automatically provide exposure information to a database maintained by the system. The collected data can be analyzed and management information provided as to gas exposures and locations in the region being monitored. One such system has been marketed by Sperian Protection Instrumentation, LLC, a Honeywell Company under the trademark, IQ SYSTEM.

BRIEF DESCRIPTION OF THE DRAWINGS

FIGS. 3A and 3B is a screen illustrating an exemplary instrument usage report;

FIG. 4 is a screen illustrating an exemplary alarm report; and

FIG. 5 is a screen illustrating an exemplary alarm event.

DETAILED DESCRIPTION

Figure 1:
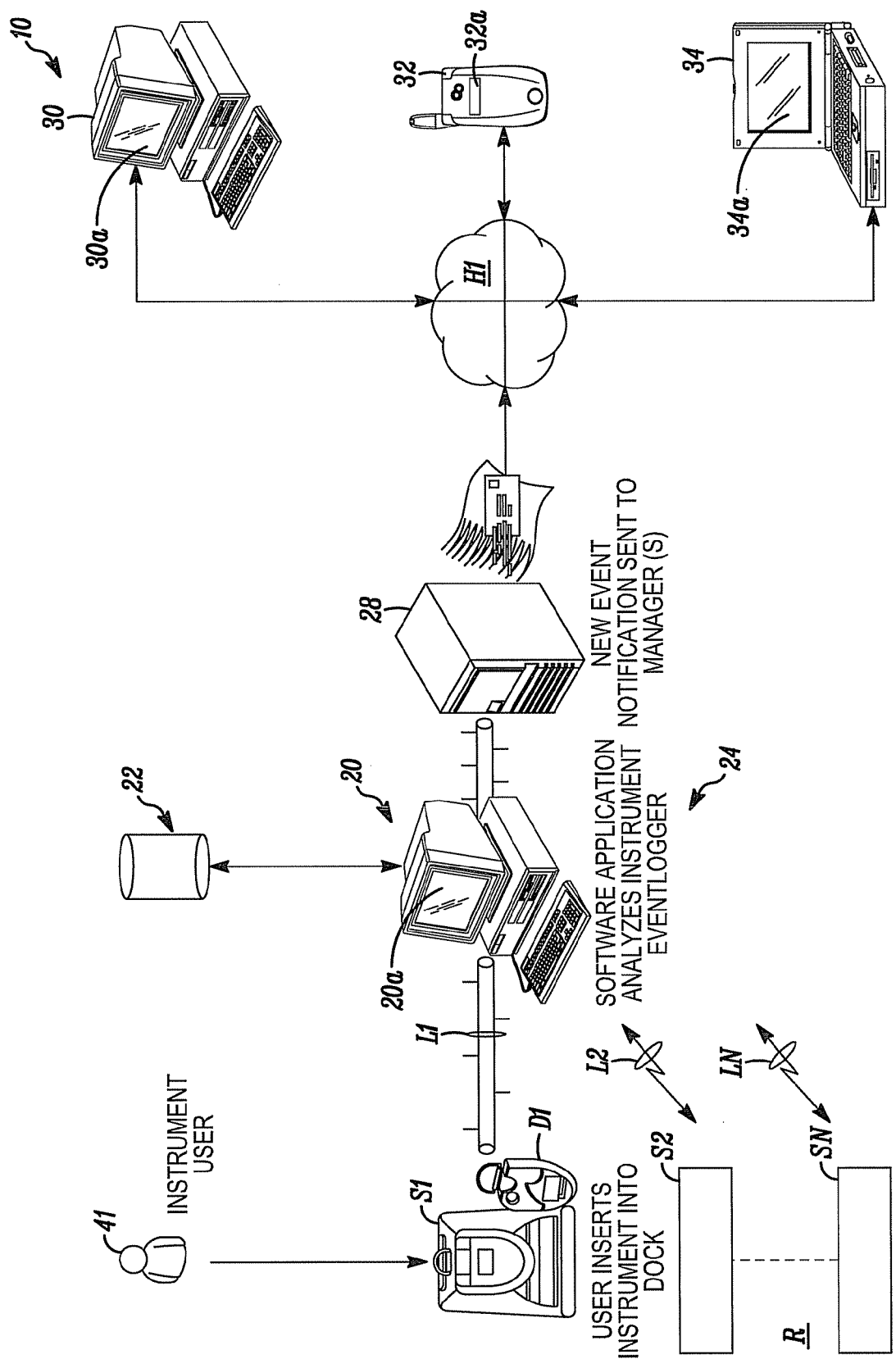
FIG. 1 illustrates a block diagram of a system in accordance herewith.

While disclosed embodiments can take many different forms, specific embodiments thereof are shown in the drawings and will be described herein in detail with the understanding that the present disclosure is to be considered as an exemplification of the principles thereof as well as the best mode of practicing same, and is not intended to limit the application or claims to the specific embodiment illustrated.

In one aspect, embodiments hereof can keep track of all gas detector assignments to a single worker. Further, gas exposure by a worker can be tracked during detector assignment.

In yet another aspect, the system can require workers to return a gas detector in an alarmed state to a docking station. Data or information as to the state of the detector and individual exposure levels can be extracted from the detector and downloaded to a data base for analysis. Reports or alarm indicating screens or messages can be created and forwarded to management in the event of gas exposure.

In another aspect, a detector can be assigned to a single user. This assignment can be changed at any time.

Advantageously, the gas detectors can incorporate an alarm latching feature. A latched alarm will continue to display an alarm condition even if the gas level drops below the defined alarm level. In another aspect, this feature can be configured to only allow the alarm latch to be reset by a docking station.

The docking station can analyze the detector's event logger and determine based on system configuration if an automatic notification needs to be generated alerting management of the exposure level. The system can also include reporting software that can generate reports on instrument usage and worker gas exposure.

In yet another aspect, an additional alarm level can be provided which exceeds the danger alarm to help define special gas events. Such events could include, without limitation, detector over range, or a user who was wearing special respiratory equipment and could work in much higher gas levels than would normally be the case. If the new alarm level is reached, all session data and event can be downloaded via the docking station.

In summary, systems in accordance herewith can promptly and automatically notify safety personnel in the event of excessive gas exposure by taking advantage of the alarm latching feature in the gas detectors. For example, E-mail notifications can be provided to safety personnel once the respective gas detector is inserted into the docking station. The latching feature is especially useful in this regard, as it only allows a reset of the detector when it is inserted into the docking station, and at that time that data can be downloaded and promptly forwarded by E-mail, or text messaging in other aspects, reports can be generated listing detector users and locations of use. Detector assignments can also be reported. Separate event generation can be provided for each alarm level including the above noted additional alarm level.

FIG. 1 is an over-all view of an apparatus 10, a gas detector management and notification system, which embodies the above. The apparatus 10 includes a plurality of docking stations S1 . . . Sn. The stations S1 are distributed throughout a region R where on-going monitoring of one or more ambient conditions, for example concentration of a selected gas, is taking place.

The docking stations, such as station S1 slidably receive a compatible gas detector, such as D1 which an instrument user 41 might have been wearing while working in the region R. It will be understood that a plurality of detectors Di might be in use simultaneously in the region R. Since in some instances the gas concentration(s) in the region R must be closely monitored to limit exposure by individuals, or instrument users in the region R, having the stations S1 available throughout the region R enables the instrument users, such as 41 to promptly provide excess concentration information to the system 10 via a local docking station such as S1. Subsequently, the management system 10 can, as described below, automatically provide messages or gas concentration alerts to displaced safety personnel.

A variety of information can be extracted from a gas detector such as D1 by the respective station S1. Such data or information can include maximum concentration level to which the user 41 has recently been exposed, periodic sensed concentration levels, individual to whom the detector has been assigned. The detector's entire event logger can be downloaded to the docking station. The docking station, responsive to the logged events, can determine if a notice or event indicating message needs to be generated and sent to a safety officer.

The docking stations S1 can each communicate via one or more wired or wireless communications links L1 . . . Ln. Those of skill will understand that the stations S1 could all communicate via a network, such as a local area network with an analysis computer 20, and associated database 22. The computer 20 can execute a software application to analyze the contents of the event logger for detector D1.

A communications server 28 can send one or more event notification messages via a computer network, such as internet I, or via a cellular-type wireless system to one or more displaced receivers such as computer 30, smart phone, PDA or the like 32 or laptop 34, all without limitation. Results of the analysis by software 24 can also be transmitted to one or more of those units.

Figure 2A:
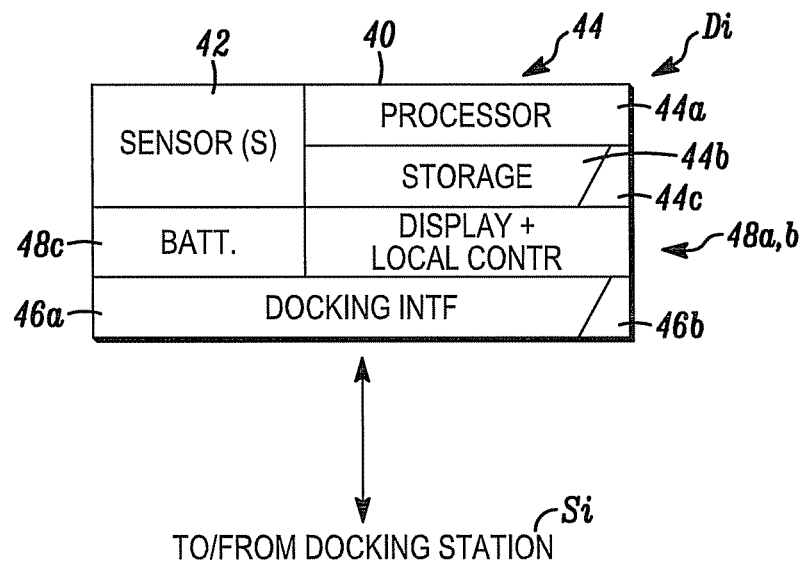
FIG. 2a is a diagram which illustrates additional details of a representative gas detector.

FIG. 2A illustrates added details of representative gas detector Di. Detector Di includes a housing 40. The housing 40 carries one or more sensors 42 which can respond to one or more selected airborne gases. The plurality of sensors 42 can also respond to smoke, humidity or the like all without limitation.

The housing 40 also carries control circuits which would be implemented at least in part with a programmable processor 44a, and associated storage circuits 44b. The circuits 44b can store executable control programs for Di along with acquired data as to gas concentrations and the like. A maximum sensed concentration can be stored, as in 44c for later downloading while the detector Di continues monitoring the local ambient concentrations.

Interface circuits 46a for communication with a docking station, such as S1, are coupled to control circuits 44. Alternate wired or wireless interfaces 46b could be provided, without limitation for communication with other devices. The housing 40 can also carry a local display device 48a, manually operable local controls 48b and a battery 48c to power the detector Di.

Those of skill will understand that the detector Di has a form factor and associated connector elements associated with the housing 40 to slidably engage the docking station S1. The control circuits 44 can communicate information to an engaged docking station, such as S1.

Figure 2B:
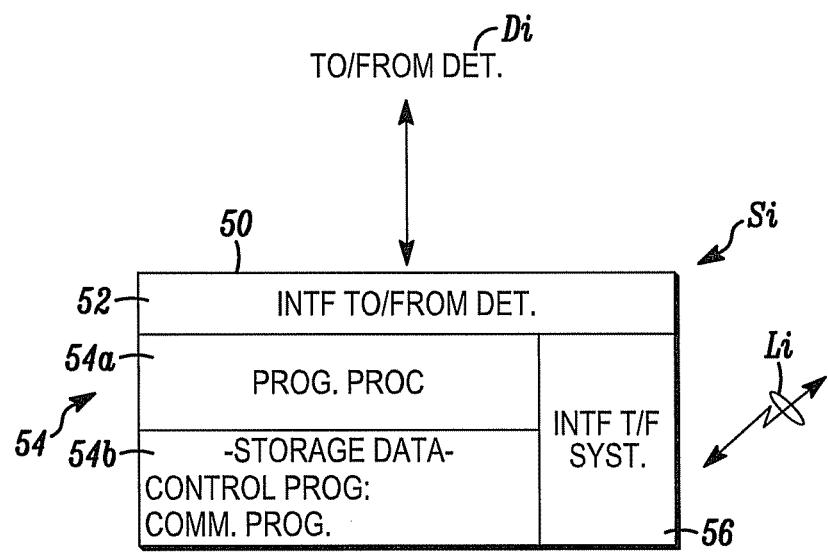
FIG. 2b is a diagram which illustrates additional details of a representative docking station.

FIG. 2B illustrates added details of representative docking station Si. Docking station Si includes a housing 50. The housing 50 carries inter face circuitry 52 to communicate with and download information from an engaged detector, such as Di. Those of skill will understand that the docking station Si has a form factor and associated connector elements associated with the housing 50 to slidably engage the detector Di.

Docking station Si also includes control circuits 54 which can be implemented at least in part with a programmable processor 54a and associated storage devices 54b. The storage devices 54b can contain executable control programs, as well as downloaded data, from detector Di, and communications programs. Information can be coupled from the docking station Si, including the maximum concentration value 44c, from detector Di, to storage and analysis computer 20, via communications link Li. The docking station Si can automatically unlatch or delete the stored maximum concentration value 44c from the storage unit 44b when information from the detector Di has been downloaded for analysis.

Advantageously, the latched maximum concentration value 44c can be automatically transmitted from computer 20 via server 28 to one or more displaced safety monitoring units such as 30-34 to alert safety officers of a need to conduct an investigation.

The analysis computer 24 can present on display 20a, or forward to units 30-34 additional tabular information as to the conditions in the region R, or the plurality of detectors being used to monitor that region.

FIGS. 3A and 3B is an exemplary instrument usage report screen 70, sorted by detector serial number and date, generated by the analysis computer 20, and software 24 and displayable on one or more of the display units 20a, 30a, or 34a.

FIG. 4 is an Alarm Report screen 80 showing Alarm Events occurring during a user configurable time line and displayable on one or more of the display units 20a, 30a, or 34a.

FIG. 5 is an Alarm Event screen 90 showing event type, min and max gas levels, and durations displayable on one or more of the display units 20a, 30a, 32a, or 34a.

From the foregoing, it will be observed that numerous variations and modifications may be effected without departing from the spirit and scope hereof. It is to be understood that no limitation with respect to the specific apparatus illustrated herein is intended or should be inferred. It is, of course, intended to cover by the appended claims all such modifications as fall within the scope of the claims. Further, logic flows depicted in the figures do not require the particular order shown, or sequential order, to achieve desirable results. Other steps may be provided, or steps may be eliminated, from the described flows, and other components may be added to or removed from the described embodiments.

The invention claimed is:

1. An apparatus comprising:
at least one ambient condition detector which includes circuitry that provides a stored, maximum sensed concentration indicator value, wherein the at least one ambient condition detector is selected from a class which includes at least one gas detector;
a docking station, releasably coupleable to the at least one ambient condition detector, the docking station includes control circuitry to receive and store selected information from the at least one ambient condition detector, and to acquire and reset the stored maximum sensed concentration indicator value in the at least one ambient condition detector and to determine whether to transmit a message to a displaced site remote to the at least one ambient condition detector; and
a communications element, coupled to the docking station, wherein the communications element comprises circuits to assign the at least one ambient condition detector to a single predetermined individual and further includes data storage to receive and store information identifying the at least one ambient condition detector, information identifying the single predetermined individual to which the at least one ambient condition detector is assigned, and the maximum sensed concentration indicator value, from the docking station wherein the communication element, responsive to the maximum sensed concentration indicator value received from the docking station from the at least one ambient condition detector when coupled thereto, transmits the message to the displaced site providing the information identifying the at least one ambient condition detector, the single predetermined individual and the maximum sensed concentration indicator value.

2. An apparatus as in claim 1 where the communications element receives and stores concentration exposure information for the at least one ambient condition detector along with the information identifying the individual to which the at least one ambient condition detector is assigned.

3. An apparatus as in claim 1 where a message indicating a sensed concentration of gas exposure exceeding a predetermined threshold concentration is transmitted to a remote location monitoring for excess ambient condition concentrations in a selected region.

4. An apparatus as in claim 3 which includes a data base, coupled to the communications element, to receive and store information from a plurality of gas detectors monitoring a selected region R.

5. An apparatus as in claim 1 where the at least one ambient condition detector comprises circuitry to latch and store the maximum sensed gas concentration indicator value.

6. An apparatus as in claim 1 which includes a plurality of ambient condition detectors and a plurality of docking stations with the docking stations coupled to the communications element, and, wherein each of the plurality of ambient condition detectors includes circuitry to only release the respective stored maximum sensed concentration indicator value in response to engaging and communicating with a respective docking station of the plurality of docking stations.

7. An ambient condition detector management system comprising:
 a plurality of ambient condition detectors;
 a plurality of detector docking stations wherein the plurality of ambient condition detectors are releasably engageable with a respective detector docking station of the plurality of the detector docking stations;
 a transmission system coupled to the plurality of detector docking stations;
 wherein the plurality of detector docking stations each include a processor and at least one memory device that stores assignment identification information to identify a respective one of the plurality ambient condition detectors to a single predetermined individual, a maximum sensed concentration indicator value, and further includes storing a plurality of instructions which when executed by the processor causes the processor to download sensed condition information, to reset the stored maximum sensed concentration indicator value of the respective ambient condition detector of the plurality of ambient condition detectors and to determine whether to transmit a message to a displaced site remote to the respective ambient condition detector of the plurality of the ambient condition detectors, providing the information identifying the at least one ambient condition detector, the single predetermined individual and the maximum sensed concentration indicator value.

8. A detector management system as in claim 7 wherein each of the plurality ambient condition detectors includes circuitry to store an indicium indicative of the maximum sensed concentration indicator value.

9. A detector management system as in claim 8 where the plurality of ambient condition detectors each include a local processor and at least one memory device that stores a plurality of instructions which when executed by the local processor causes the local processor to store the indicium indicative of the maximum sensed concentration indicator value at the respective ambient condition detector.

10. A method comprising:
 sensing a plurality of ambient conditions by a plurality of ambient condition detectors each spaced apart in different locations in a region being monitored;
 storing an indicator of a maximum gas concentration indicator value associated with at least some of the locations by respective ambient condition detectors of the plurality of ambient condition detectors associated with respective locations, and further storing assignment identification information to identify the respective ambient condition detectors of the plurality of ambient condition detectors to a single predetermined individual respectively, by respective detector docking stations of the respective ambient condition detectors;
 forwarding each of the stored indicators, by the respective ambient condition detectors of the plurality of ambient condition detectors, via docking to the respective detector docking stations at the respective initial analysis locations, and responsive to initial analysis at the respective initial analysis locations, resetting the stored indicators by the respective detector docking stations of the respective ambient condition detectors, and forwarding all of the stored indicators from the respective initial analysis locations, to a common collection location by respective detector docking stations, wherein the common collection location comprises a communications element coupled to the respective detector docking stations of the respective ambient condition detectors to receive the stored indicators;
 determining at the common location whether to send at least one emergency message indicating a sensed concentration of gas exposure exceeding a predetermined threshold concentration and the assignment identification information for each respective ambient condition detector of the plurality of ambient condition detectors, respectively, by the communications element; and
 storing the initial analysis locations at the common location while forwarding the at least one emergency indicting message therefrom to a displaced monitoring site indicative of at least one of the stored indicators, by the communications element providing the information identifying the at least one ambient condition detector, the single predetermined individual and the maximum sensed concentration indicator value, respectively.

\* \* \* \* \*